(12) United States Patent
Cardinale et al.

(10) Patent No.: US 9,820,840 B2
(45) Date of Patent: Nov. 21, 2017

(54) TEMPORARY AIDS FOR DEPLOYMENT AND FIXATION OF TISSUE REPAIR IMPLANTS

(71) Applicant: Ethicon, Inc., Somerville, NJ (US)

(72) Inventors: Michael Cardinale, Morristown, NJ (US); Anthony Worthington, East Falmouth, MA (US); Robert J. Tannhauser, Bridgewater, NJ (US); Emil Richard Skula, Wayne, NJ (US)

(73) Assignee: Ethicon, Inc., Somerville, NJ (US)

( * ) Notice: Subject to any disclaimer, the term of this patent is extended or adjusted under 35 U.S.C. 154(b) by 98 days.

(21) Appl. No.: 14/641,805

(22) Filed: Mar. 9, 2015

(65) Prior Publication Data

US 2015/0173882 A1    Jun. 25, 2015

Related U.S. Application Data

(62) Division of application No. 13/628,500, filed on Sep. 27, 2012, now Pat. No. 9,005,223.

(51) Int. Cl.
| | | |
|---|---|---|
| *A61F 2/00* | (2006.01) | |
| *A61B 17/10* | (2006.01) | |
| *A61B 17/08* | (2006.01) | |
| *A61B 17/068* | (2006.01) | |
| *A61B 17/00* | (2006.01) | |

(Continued)

(52) U.S. Cl.
CPC ........ *A61F 2/0063* (2013.01); *A61B 17/0057* (2013.01); *A61B 17/068* (2013.01); *A61B 17/08* (2013.01); *A61B 17/10* (2013.01); *A61B 2017/00637* (2013.01); *A61B 2017/00659* (2013.01); *A61B 2017/0647* (2013.01); *A61B 2090/0807* (2016.02); *A61F 2002/0072* (2013.01)

(58) Field of Classification Search
CPC ............ A61F 2/0063; A61F 2002/0068; A61F 2002/0072; A61F 2002/30093; A61F 2210/0019; A61B 17/0057; A61B 17/068; A61B 17/08; A61B 17/10; A61B 17/00234; A61B 2090/0807; A61B 2017/0647; A61B 2017/00659; A61B 2017/00637; A61B 2017/00575; A61B 2017/081; A61B 2090/0811
See application file for complete search history.

(56) References Cited

U.S. PATENT DOCUMENTS

| | | | |
|---|---|---|---|
| 5,370,650 A | | 12/1994 | Tovey et al. |
| 5,397,331 A | * | 3/1995 | Himpens ............ A61B 17/0057 |
| | | | 128/899 |

(Continued)

FOREIGN PATENT DOCUMENTS

| | | |
|---|---|---|
| EP | 0557964 | 9/1993 |
| FR | 2945931 | 6/2009 |

(Continued)

*Primary Examiner* — Jocelin Tanner
(74) *Attorney, Agent, or Firm* — E. Richard Skula

(57) ABSTRACT

Novel deployment devices for use as adjuncts with tissue repair implants. The devices are removeably mounted to mesh tissue repair implant devices to manipulate the devices into position and provide for secure fixation about the periphery of such mesh implant devices by providing guide structures such as grooves for directing and positioning a surgical tacking instrument.

5 Claims, 14 Drawing Sheets

(51) Int. Cl.
 *A61B 17/064* (2006.01)
 *A61B 90/00* (2016.01)

(56) References Cited

U.S. PATENT DOCUMENTS

| | | | |
|---|---|---|---|
| 6,174,320 B1* | 1/2001 | Kugel | A61F 2/0063 606/151 |
| 6,610,006 B1* | 8/2003 | Amid | A61F 2/0063 600/37 |
| 2003/0004581 A1* | 1/2003 | Rousseau | A61F 2/0063 623/23.74 |
| 2004/0073257 A1 | 4/2004 | Spitz | |
| 2005/0288691 A1* | 12/2005 | Leiboff | A61F 2/0063 606/151 |
| 2008/0195121 A1* | 8/2008 | Eldar | A61B 17/00234 606/151 |
| 2009/0254103 A1* | 10/2009 | Deutsch | A61F 2/2481 606/151 |
| 2010/0069930 A1 | 3/2010 | Roslin et al. | |
| 2010/0069947 A1* | 3/2010 | Sholev | A61B 17/00234 606/192 |
| 2011/0054500 A1 | 3/2011 | Levin et al. | |
| 2011/0118706 A1* | 5/2011 | Gingras | A61B 17/00234 606/1 |

FOREIGN PATENT DOCUMENTS

| | | |
|---|---|---|
| WO | WO 2008/065653 | 6/2008 |
| WO | WO 2009/027542 | 3/2009 |

\* cited by examiner

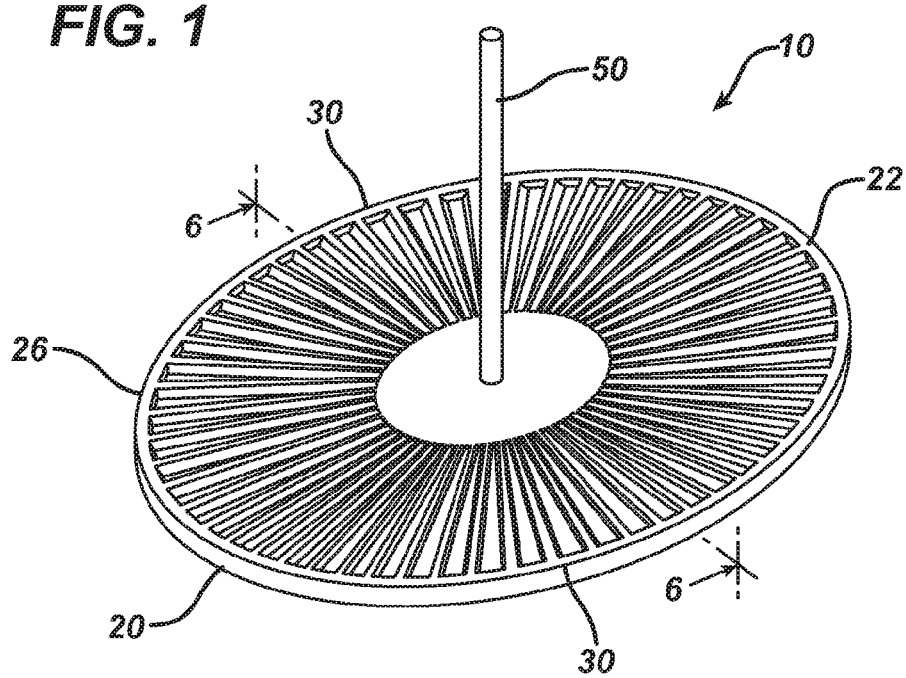
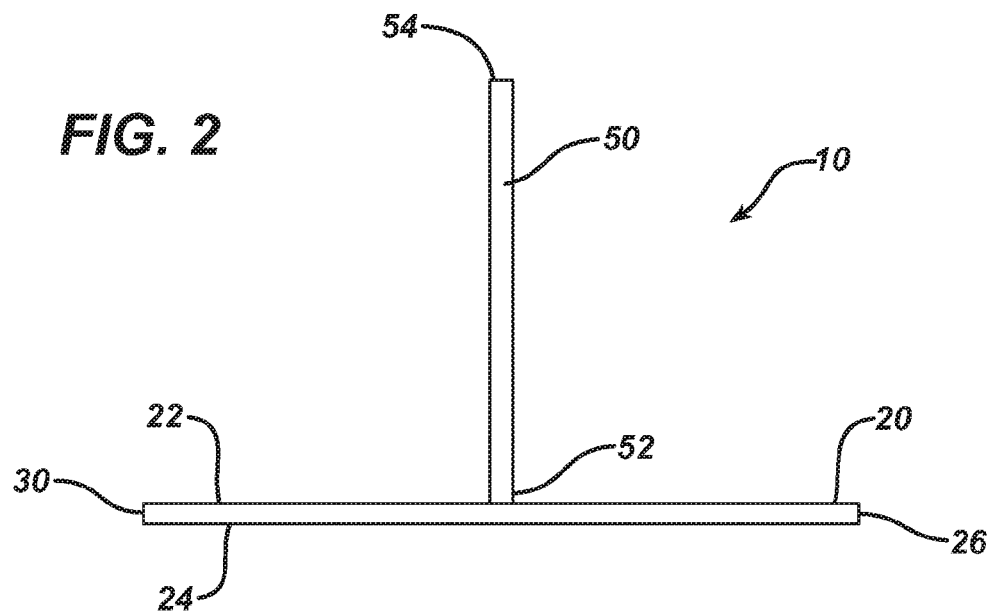

TEMPORARY AIDS FOR DEPLOYMENT AND FIXATION OF TISSUE REPAIR IMPLANTS

CROSS-REFERENCE TO RELATED APPLICATION

This application is a divisional of co-pending application Ser. No. 13/628,500 filed on Sep. 27, 2012.

TECHNICAL FIELD

The field of art to which this invention relates is medical devices, more particularly, medical devices useful as tissue repair implants.

BACKGROUND OF THE INVENTION

Body wall defects such as hernias and trocar punctures are typically repaired by implanting surgical mesh patch implants at the site of the body wall defect. The mesh patch implants are secured to the surrounding tissue in a conventional manner including tacking, suturing, gluing, etc. A surgical mesh implant is typically constructed to have one or more layers of a porous surgical mesh shaped to conform to the body wall defect in order to provide for optimal securement. The mesh implants must also be designed to promote sufficient tissue ingrowth such that the body wall defect repair is incorporated into the body wall tissue to provide superior strength and durability. Another desired attribute of a tissue repair implant is that it have softness and flexibility, along with minimal mass in order to provide the patient with the requisite post-operative comfort.

Since tissue repair implants are typically made from surgical meshes or fabrics that are flexible, the implants may present deployment issues to the surgeon during the course of a surgical repair procedure, when it is necessary to insert the mesh into a patient's body cavity and then appropriately affix the mesh implant to secure it in place in order to effect the repair of the tissue defect. Typically, the mesh in its relaxed configuration will be significantly larger than the size of the defect and the size of the opening in the patient through which the mesh is introduced. The mesh implant is usually folded or rolled by the surgeon in order to introduce it to a location adjacent to the tissue defect. It must be then unfolded or unrolled to its at-rest planar configuration to allow for fixation. The mesh repair implant must then be moved into place adjacent to the body wall so that it can be fixated in a conventional manner using tacks, sutures, etc. Those skilled in this art will appreciate the difficulties in moving and fixating a soft, low mass, flexible mesh implant during a surgical repair procedure. The difficulties are significantly enhanced in minimally invasive surgeries.

In order to improve the handling characteristics of mesh implants, devices have been developed that urge the mesh implant into a planar configuration after insertion into the patient's body. In the case of mesh implants for open procedures, elastic supports such as monofilament rings have been sewn into the mesh implants. However, it is known that these support structures may fail in vivo leading to life threatening complications and severe patient pain and discomfort. Instruments have also been developed to deliver tissue repair implants to a tissue defect site. The instruments typically have manipulatable fingers or members that maintain the mesh in a substantially planar position at the defect site; and, after the implant is affixed to the defect site the fingers or members are withdrawn into the delivery instrument and the instrument is removed. Such instruments also have disadvantages. The fingers or members may injure tissue or viscera causing a variety of complications, and the instruments may fail in use and not properly function to maintain the mesh implant in a planar position, or may fail to release the implant. In addition, the instruments are typically disposable, and, are expensive, thereby adding to the cost of the procedure.

In many open tissue defect procedures, it is necessary to utilize a skirted mesh device or a device having a pocket in order to provide an accessible structure for affixing the device securely to the inner wall of the body cavity (e.g., the peritoneum and fascia), since the surgeon is not able to affix the mesh from the visceral side of the device. In an endoscopic procedure, the surgeon can view the visceral side of the tissue repair patch remotely via an endoscopic camera system, and precisely guide a fixation instrument to fixate the device about the periphery and interior to the periphery in a multiple crown fixation pattern. In an open procedure this is typically not possible and the surgeon must guide the end of a fixation device by estimating the position of the periphery of the mesh device and by palpating the patient's skin to determine the location. This technique may have several deficiencies associated with it. As mentioned previously, in order to have an adequate repair with the best prospects for proper healing it is necessary to secure the mesh implant such that the mesh is placed as close and flush to the surface of the interior body wall as possible. If the mesh is not secured uniformly to body tissue about its periphery, the mesh may wrinkle or otherwise deform leaving sections of the mesh elevated above the surface of the body wall. This type of installation will not provide an optimal surgical or patient outcome, and revision surgery may be required. In addition, the spaces between the raised section of the mesh and the body cavity wall may be prone to surgical adhesions, infections, poor tissue integration, bowel entrapment, etc., further complicating the outcome for the patient.

There is a need in this art for novel adjunct devices that may be combined with a surgical tissue repair implant such that the device urges a tissue repair implant into a planar configuration for optimal surgical affixation, but is removable after the affixation is completed. There is a further need for such a device that has features which enable the surgeon to guide the end of an affixation instrument to properly locate fasteners about the periphery of the device.

SUMMARY OF THE INVENTION

Therefore a novel deployment device for a tissue repair implant is disclosed. The deployment device has a flexible planar member. The planar member has a top surface and a bottom surface and an outer periphery. The planar member being capable of moving between a first at rest position to a second deformed position. A plurality of guide structures extend radially outward along the top of the planar member. The guide structures have inward proximal ends and outward distal ends. An optional peripheral rim about the outer periphery of the planar member acts as a stop at the distal ends of the channels. The deployment device optionally has a grasping element extending up from the planar member.

Another aspect of the present invention is the combination of a surgical mesh tissue repair implant and the novel deployment device of the present invention.

Still yet another aspect of the present invention is a method of repairing a tissue defect using the novel deployment device of the present invention.

These and other aspects and advantages of the present invention will become more apparent from the following description and accompanying drawings.

BRIEF DESCRIPTION OF THE DRAWINGS

FIG. 1 is a perspective view of an embodiment of a deployment device of the present invention.

FIG. 2 is a side view of the deployment device of FIG. 2.

DETAILED DESCRIPTION OF THE INVENTION

Figure 3:
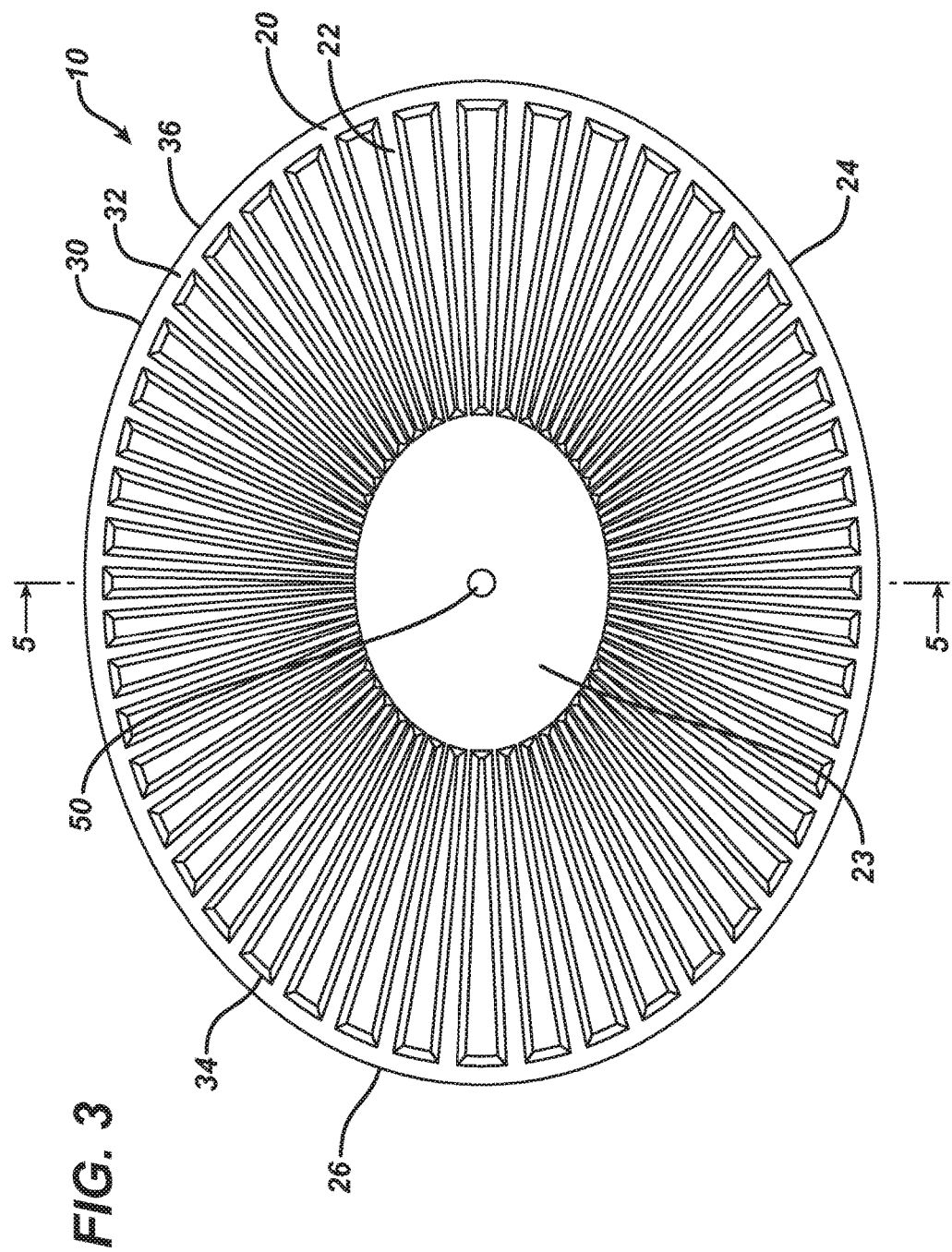
FIG. 3 is top or plan view of the deployment device of FIG. 1.
Figure 4:
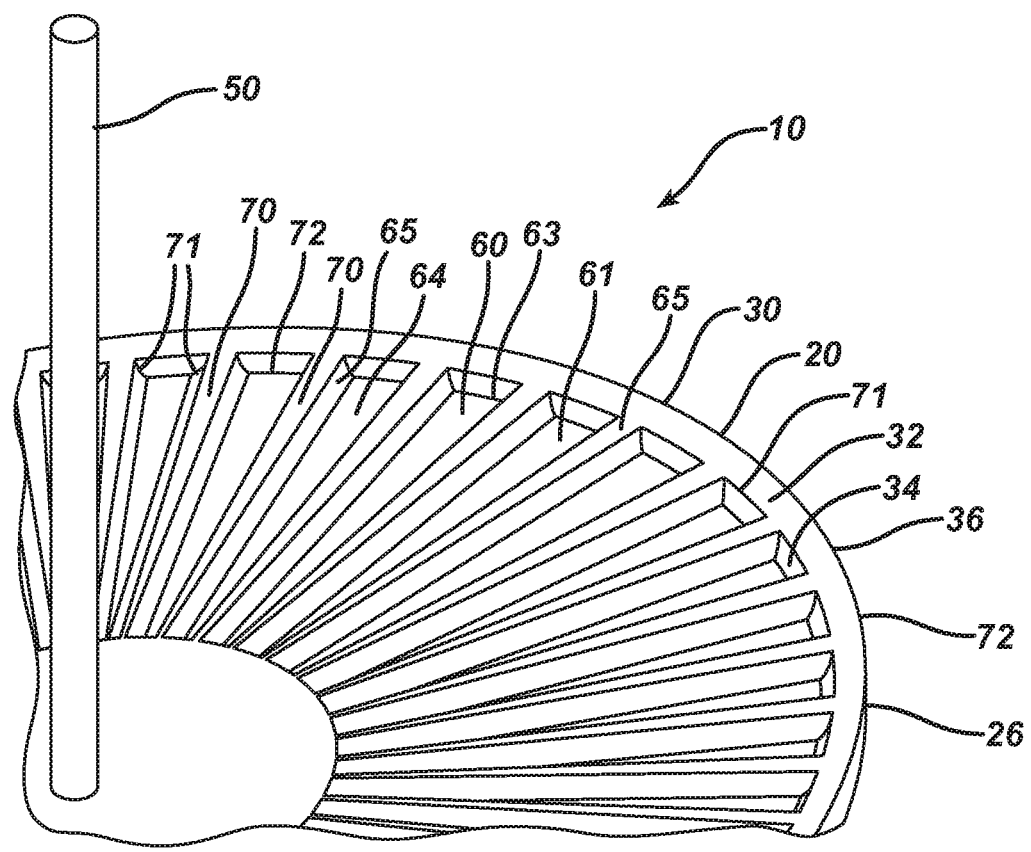
FIG. 4 is a partial magnified perspective view of a section of the deployment device of FIG. 1.
Figure 5:
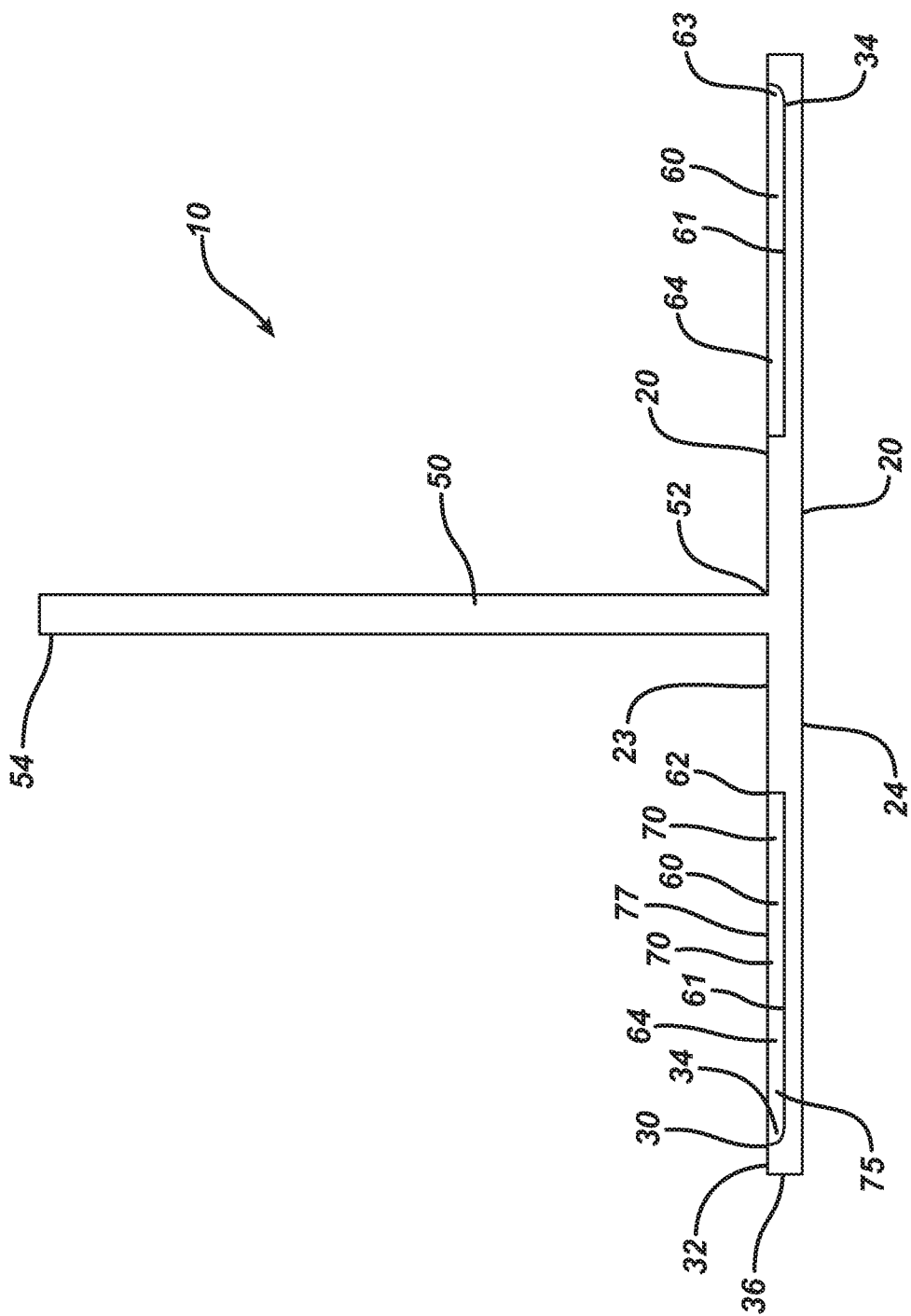
FIG. 5 is a cross-sectional view taken along ViewLine 5-5 of device of FIG. 3.
Figure 6:
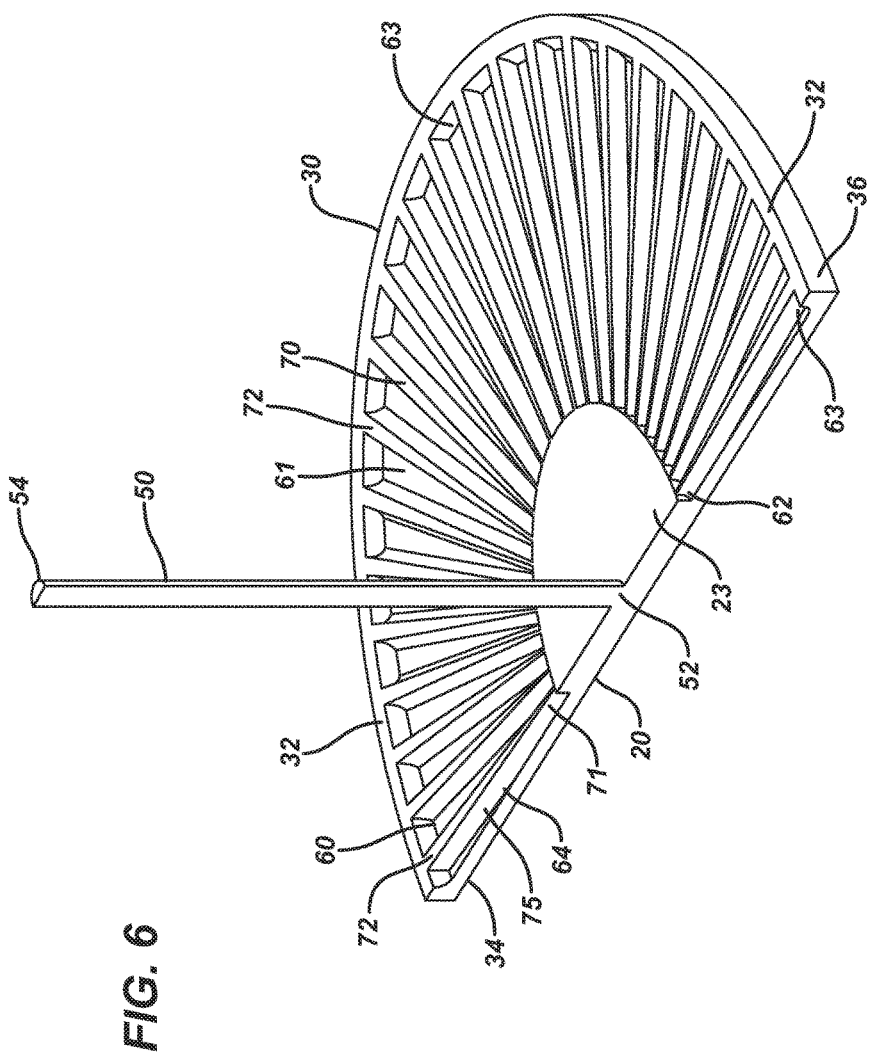
FIG. 6 is a cross-sectional perspective view taken along ViewLine 6-6 of the device of FIG. 1.

The deployment devices of the present invention may be constructed from any conventional biocompatible materials that provide sufficiently effective rigidity and flexibility, as well as ease of manufacture. The materials include conventional absorbable and nonabsorbable polymeric materials. The nonabsorbable polymeric materials include polyolefins, polytetrafluoroethylene, nylon, silk, thermoplastics, elastomers, and other polymeric materials that are sufficiently thin to promote flexibility, and the like. The absorbable polymeric materials include polylactides (PLA), polyglycolides (PGA), polydioxanones (PDO, PDS), copolymers of PGA/ trimethylene carbonate (TMC), polycaprolactones, copolymers of any forementioned polymers, and the like. If desired the deployment materials may be made from conventional metals and alloys including surgical stainless steel, shape memory metals such as nitinol, copper-aluminum-nickel, nickel-titanium and the like. The deployment devices may also be constructed from biocompatible composite materials including polycarbonates, polymethylmethacrylate, and the like.

The deployment devices of the present invention may be made using conventional manufacturing equipment and processes including injection molding, solvent casting, machining, cutting, cast molding, thermoforming, and the like.

Tissue repair implants and surgical instruments for applying tacks to fixate tissue repair implants are disclosed in the following commonly assigned, co-pending patent applications, which are incorporated by reference: U.S. Ser. Nos. 12/464,151; 12/464,165; 12/464,177; 12/464,143; 12/944, 651; and Ser. No. 12/815,275.

The mesh tissue repair devices that can be utilized with the novel deployment devices of the present invention include conventional tissue repair meshes having skirts or pockets that are useful in open surgical procedures to repair a tissue defect in a body wall. The meshes will typically have a bottom layer and a top layer of a conventional tissue repair materials with an access opening in the top layer. The bottom layer of the mesh may have a conventional adhesion barrier material affixed to at least part of its bottom or outer surface. The mesh materials may be conventional knitted or crocheted meshes, e-PTFE materials, woven and non-woven surgical fabrics, etc. The mesh materials may be constructed of conventional polymeric materials including polypropylene, Nylon, e-PTFE, polyester, ultra high molecular weight polyethylene, and the like. The polymeric materials may be bioabsorbable or nonabsorbable, or may consist of combinations of bioabsorbable and nonabsorbable materials. Examples of commercially available mesh implants include: ETHICON PHYSIOMESH™ and ETHICON PROCEED™ Surgical Mesh, available from Ethicon, Inc., Route 22 West, Somerville, N.J. 08876; Ventrio™ ST Hernia Patch and Ventrio™ Hernia Patch available from BARD Davol; the Parietex™ Composite Open Skirt (PCO OS) Mesh from Covidien plc; and the C-QUR TacShield™ available from Atrium Medical Corporation.

The patches and their components are preferably made from conventional biocompatible polymers that may be nonabsorbable or bioabsorbable. The term bioabsorbable is defined to have its conventional meaning and includes both biodegradable and bioresorbable. Examples of such nonabsorbable polymers include polypropylene, polyester, nylon, ultra high molecular weight polyethylene, and the like and combinations thereof. Examples of suitable bioabsorbable polymers include polylactides (PLA), polyglycolides (PGA), polydioxanones (PDO, PDS), copolymers of PGA/ trimethylene carbonate (TMC), copolymers of PLA/TMC, and the like. If desired, combinations of biocompatible nonabsorbable polymers and bioabsorbable polymers may be utilized to construct the tissue repair implant patch devices of the present invention.

Referring now to FIGS. 1-14, an embodiment of a deployment device of the present invention is seen. The device 10 is seen to have planar member 20. Planar member 20 has top surface 22 and bottom surface 24. Planar member 20 is illustrated as having a substantially oval configuration, but may have other geometric configurations including circular, elliptical, square, rectangular, diamond shaped, hexagonal, polygonal, curved, combinations thereof, etc. Member 20 is seen to have optional circumferential rim member 30 extending about the periphery 26 of the planar member 20. Rim member 30 may be continuous or segmented. The rim member 30 is seen to have top 32, inner stop wall 34 and outer wall 36. If desired, the top 32 of rim member 30 may be at the same level of the surface 22, or may be higher or lower. The top surface 20 is also seen to have optional flat inner section 23. Extending from the planar member 20 is the optional manipulation member 50. Member 50 is seen to have a cylindrical rod-like configuration having proximal end 52 and free distal end 54. Member 50 may have a variety of shapes and configurations, and may be flexible or rigid. Examples include rods, finger grips, tapes, ropes, loops, handles, finger holes, straps, etc. In one embodiment, the member 20 may have an optional opening (not shown) extending through the member.

The planar member 20 is seen to have a plurality of grooves 60. The grooves 60 are seen to extend into top surface 22 and extend radially outward from the center of member 20 out to the rim member 30. The grooves 60 are seen to have bottoms 61, inner ends 62, outer ends 63, opposed sides 65, and open tops 64. Each groove contains a passage 64 for receiving at least part of a distal section of a surgical fastening instrument. The grooves are seen to have opposed radial wall members 70, having inner ends 71, side walls 75, tops 77 and distal ends 72 that abut or intersect the inner stop wall 34 of rim member 30. The grooves or guide structures 60 are seen to be contained in member 20, but may alternatively extend up from the top surface 22. The grooves 60 may also be formed from spaced apart rib members extending up from top surface 22 of planar member 20. Although not illustrated, the grooves 60 may take the form of radially extending hollow tubular members having passages for receiving a shaft of a surgical fastening instrument. The grooves are aligned at some consistent spacing, e.g., 1 cm, to ensure that the tacking instrument delivers fixation points consistently and evenly about the perimeter of the device. Optionally, the grooves 60 may have one or more circumferential guide elements or indicators. These indicators may be located radially outwardly at one or more locations within each groove to provide consistent positioning of rows of fasteners (crowns) inwardly from the outer ends 63 of the grooves 60. These tactile indicators may be raised sections, ribs, depressions, frictional irregularities, etc., which provide tactile feedback to the surgeon as the tip of the applicator is moved along the groove along the groove or guide. The indicators may extend from the bottom 61 and/or sides 65.

Figure 16:
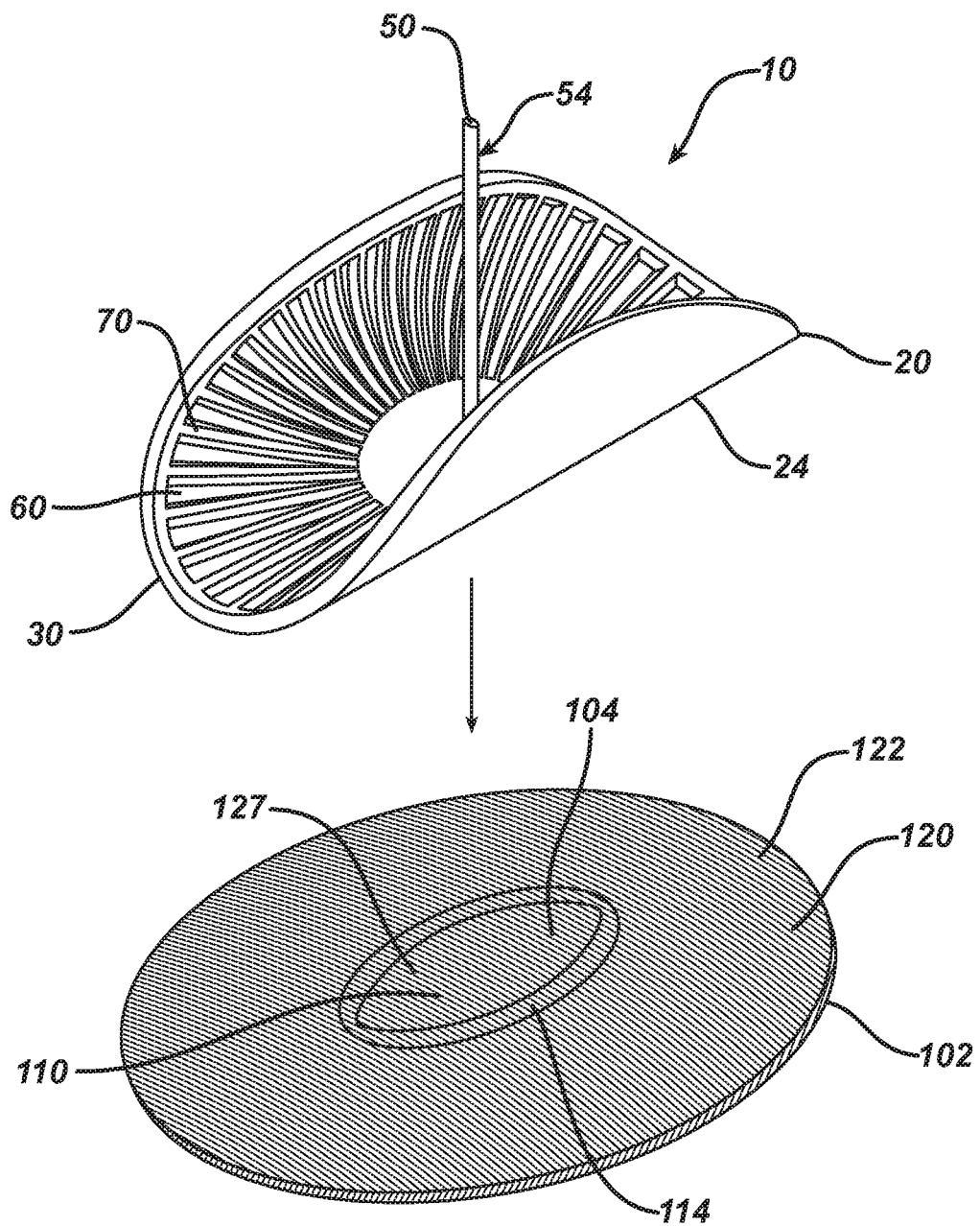
FIG. 16 is a perspective view of a deployment device of the present invention wherein the planar member is moved from the at rest position to a deployment position for insertion of the planar member though the top opening and into the pocket of a mesh repair device.

The planar member 20 is moveable between a first at-rest position and a second deployment position. In the second deployment position, the planar member 20 may be folded or otherwise manipulated such that it is insertable into the pocket of a mesh tissue repair device, such as mesh tissue repair device 100 as seen in FIG. 16. In another embodiment, not shown, a plurality of collapsible members may be affixed to the planar member 20 to collapse and move the member 20 from a first at rest position to the second deployment position, and vice versa.

Figure 7:
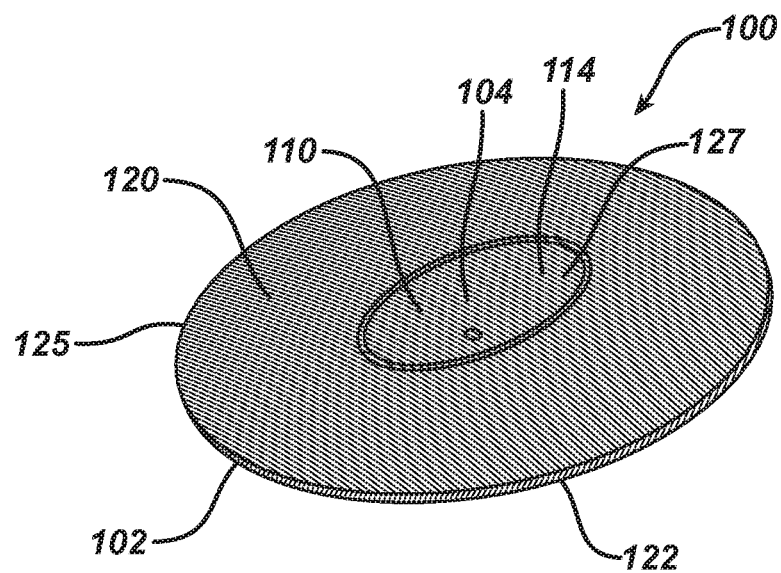
FIG. 7 is a perspective view of a dual layer mesh tissue repair device having a pocket and a tissue affixation skirt.
Figure 8:
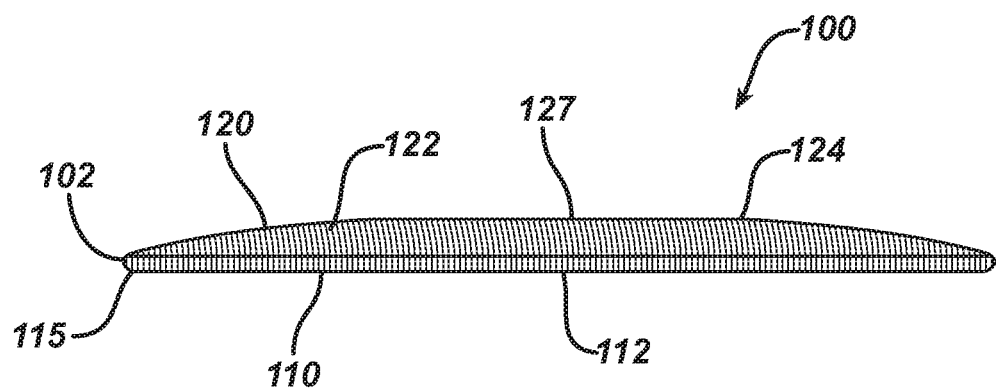
FIG. 8 is a side view of the mesh tissue repair device of FIG. 7.
Figure 9:
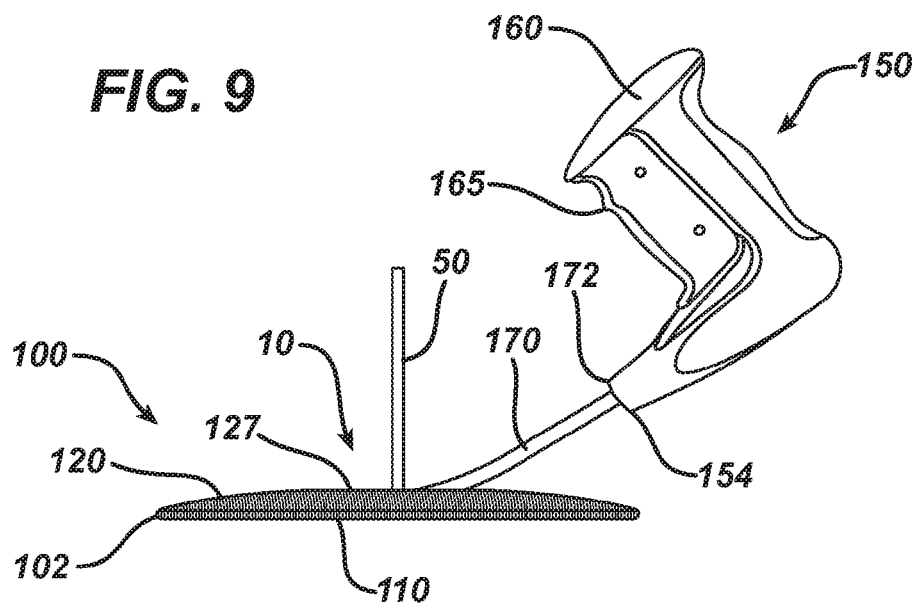
FIG. 9 is a side view of a deployment device of the present invention having the planar grooved member contained within the interior pocket of the mesh of FIG. 7; a surgical tacking instrument is illustrated having a shaft, with a distal section of the shaft being partially contained in a groove on the deployment device, and wherein the distal end of the shaft is adjacent to the end of the groove and the rim of the device.
Figure 10:
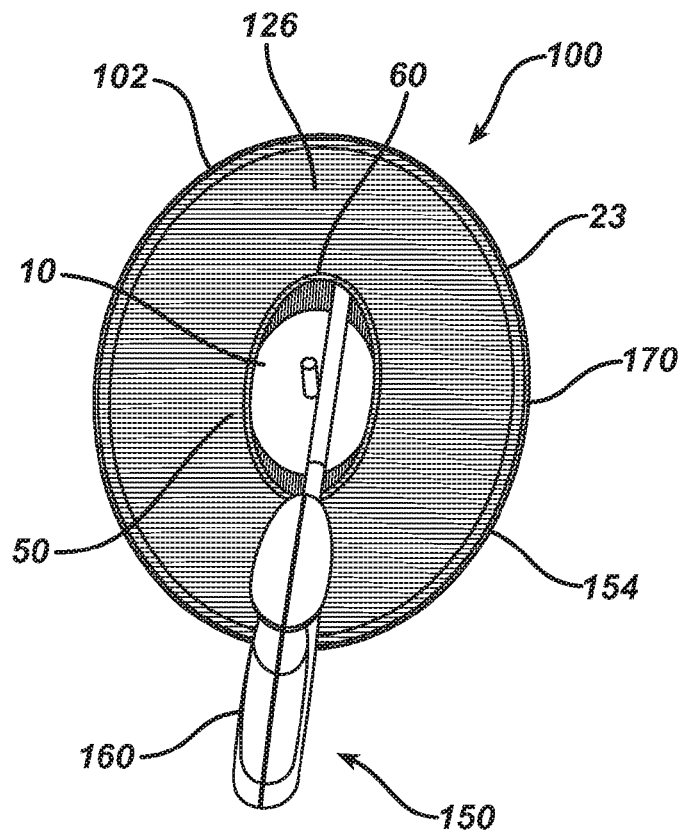
FIG. 10 is a top view of the deployment device and mesh repair device of FIG. 9.
Figure 11:
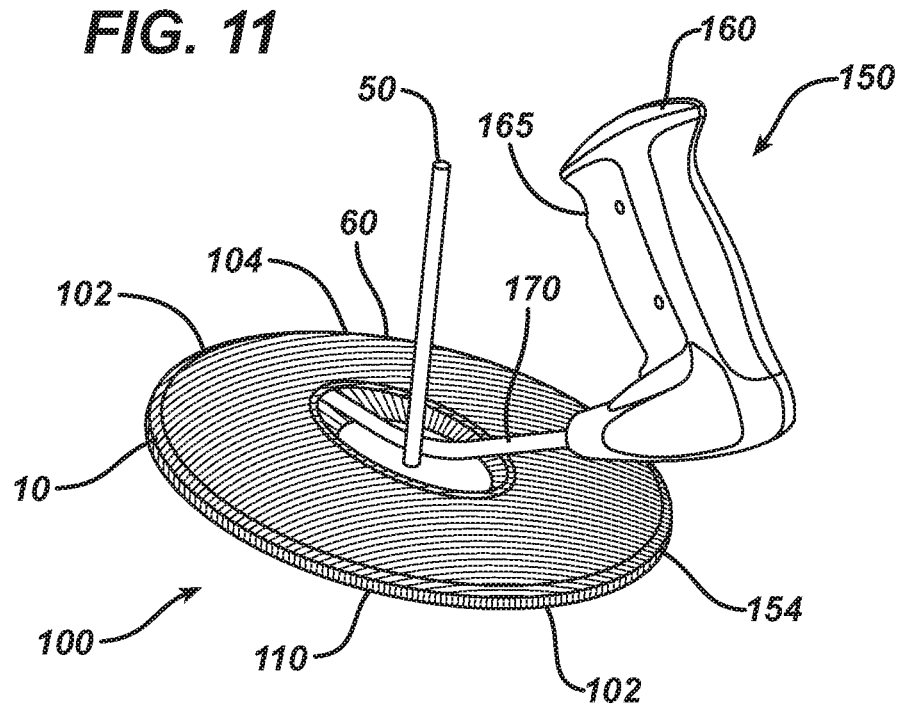
FIGS. 11 and 12 are perspective views of the deployment device, mesh repair device and tacking instrument of FIG. 9.
Figure 12:
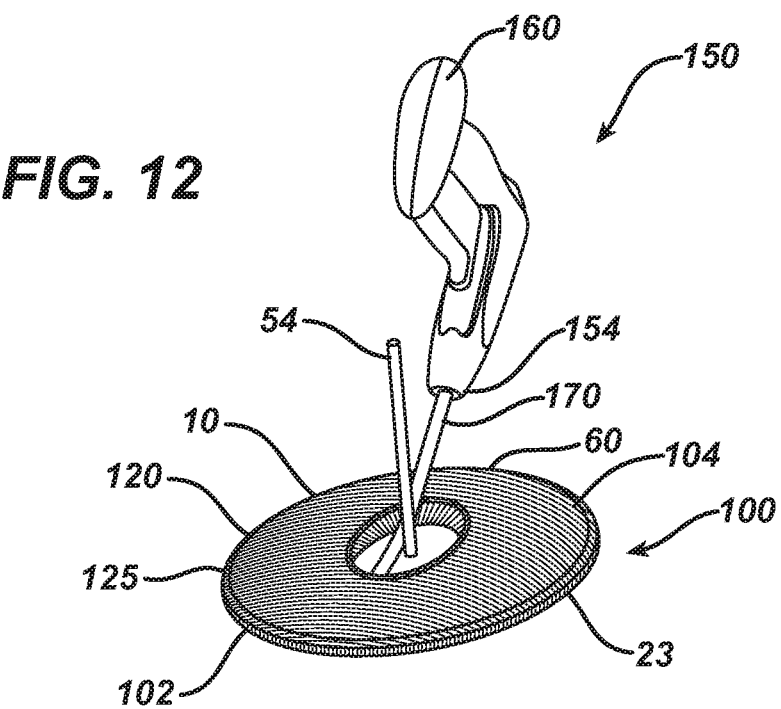
Figure 13:
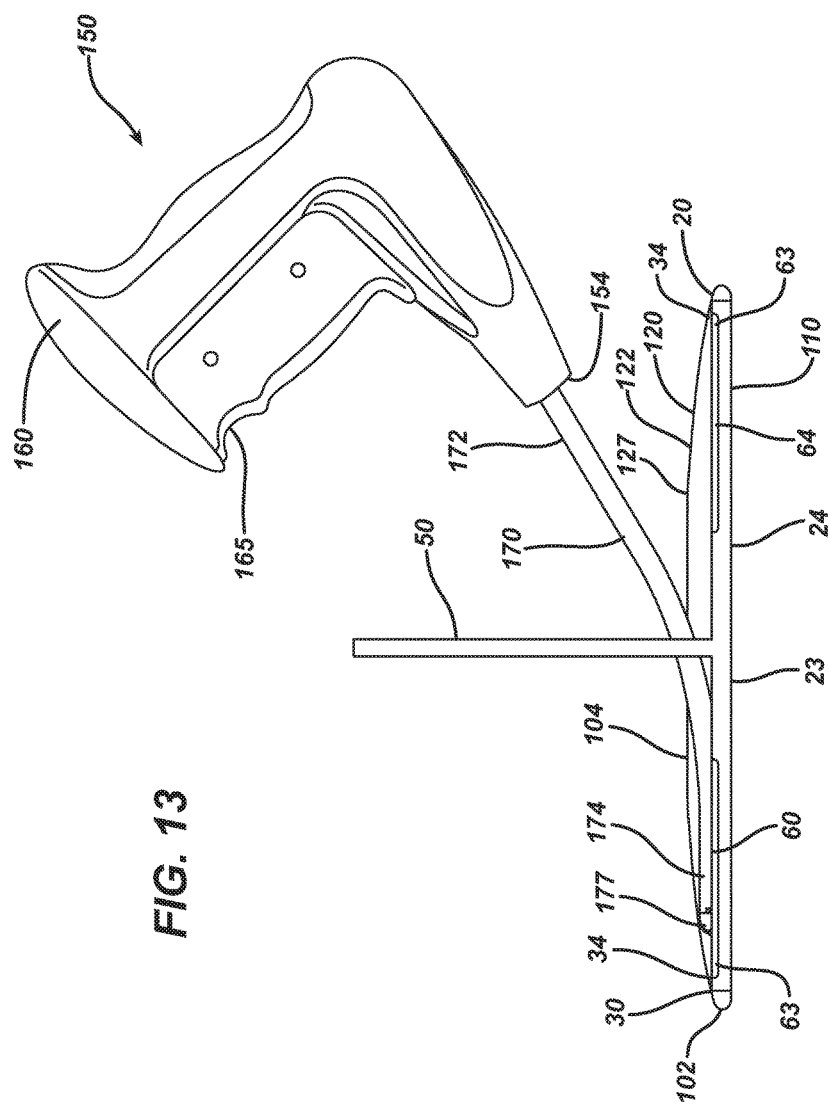
FIG. 13 is a cross-sectional view of the deployment device and mesh repair device of FIG. 9 showing the shaft of the surgical tacking instrument engaged in a groove with the distal end of the shaft proximal to the peripheries of the deployment device and the mesh repair device.
Figure 14:
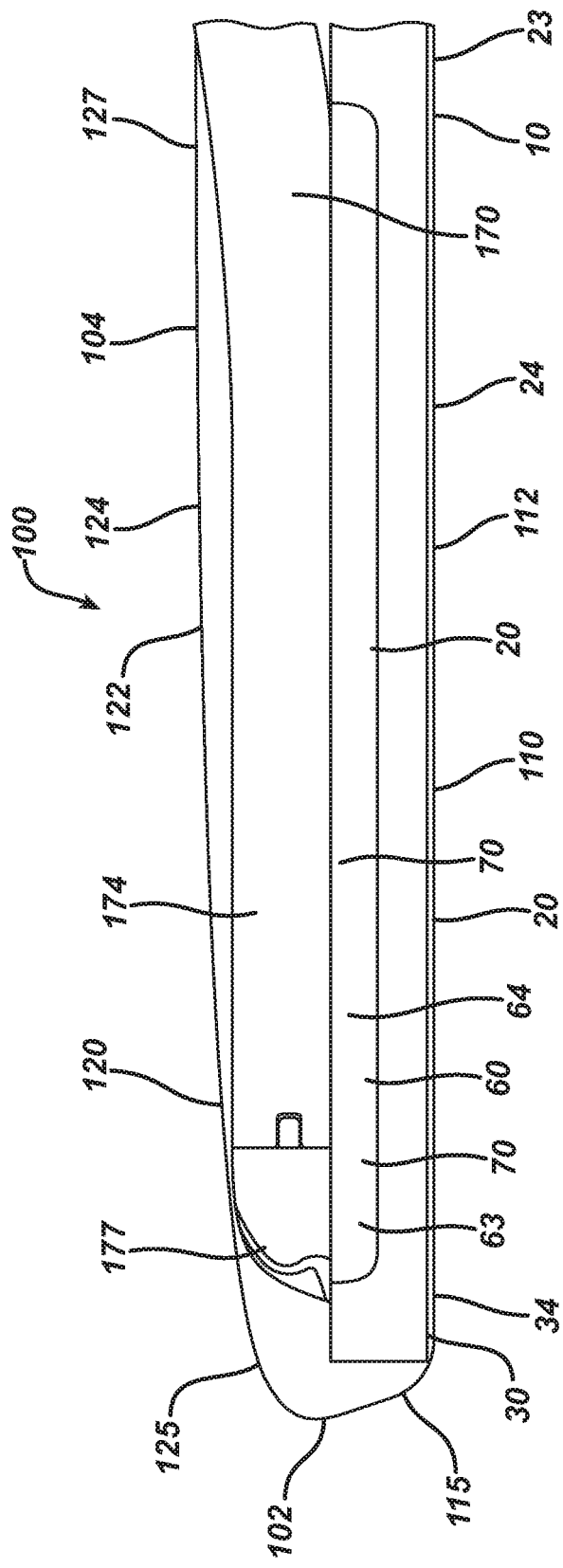
FIG. 14 is a magnified cross-sectional view of the periphery of the deployment device and mesh device of FIG. 13, illustrating the distal end of the shaft adjacent to the periphery of the skirt of the mesh device and in a position to apply tacks through the skirt into tissue.
Figure 15:
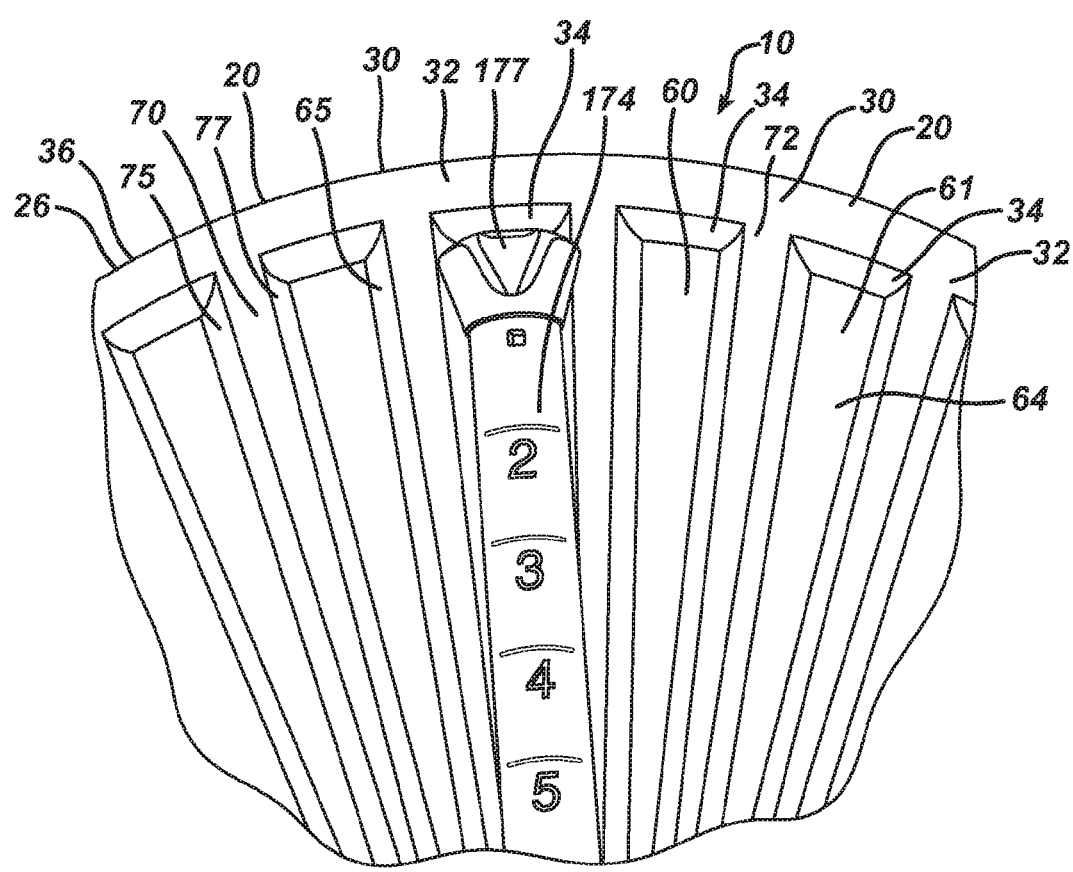
FIG. 15 is a partial magnified top view of the deployment device of FIG. 14, showing the distal end of the shaft of the fastening device in a groove adjacent to the inner wall of the rim.

A pocketed mesh tissue repair device 100 that may be utilized with the novel deployment devices of the present invention is seen in FIGS. 7 and 8. The mesh device 100 is seen to have a first or bottom layer 110 and a second or top layer 120. The mesh layer 110 is seen to have bottom 112, top 114 and outer periphery 115. Mesh layer 120 is seen to have top 122, bottom 124, outer periphery 125, and central opening 127. Layers 110 and 120 are joined about their peripheries 115 and 125 to form the device 100. Mesh repair device 100 is seen to have outer periphery 102 and interior pocket 104. The pocket 104 is accessible through opening 127. The top layer 120 forms a skirt between opening 127 and outer periphery 125, which is used to affix the mesh device 100 to tissue.

Referring now to FIGS. 9-15, a deployment device 10 of the present invention mounted to a mesh repair device 100 is seen. A surgical tacking instrument 150 is seen. Tacking instrument 150 is seen to have a proximal handle 160 having an actuation trigger 165. Extending from the distal end 154 of instrument 150 is the shaft 170, having distal end 174 and proximal end 172. The shaft 170 is seen to be curved to facilitate affixation of the skirt of top layer 120 to the tissue of an adjacent body wall. Surgical tacks are discharged through discharge tip 177 on distal end 174. Although most conventional tacking instruments may be used in conjunction with the novel deployment devices of the present invention, a particularly suitable surgical tacking instrument is disclosed in co-pending, commonly assigned U.S. patent application Ser. No. 12/944,651 and Ser. No. 13/470,022, filed on Nov. 11, 2010 and May 11, 2012 respectively which are incorporated by reference.

As seen in FIGS. 9-15, the planar member 20 of deployment device 10 has been inserted into pocket 104 of mesh tissue repair device 100 through opening 127. The shaft is partially contained in a groove 60 such that the shaft is guided toward the outer or distal end 63 of the groove 60 adjacent to the inner stop wall 34 of rim member 30. The discharge tip 177 of shaft 170 is proximate to the periphery 102 of mesh device 100. In this position a tack can be inserted from the instrument 150 through discharge tip 177 through mesh layer 120 into adjacent body tissue.

Figure 17:
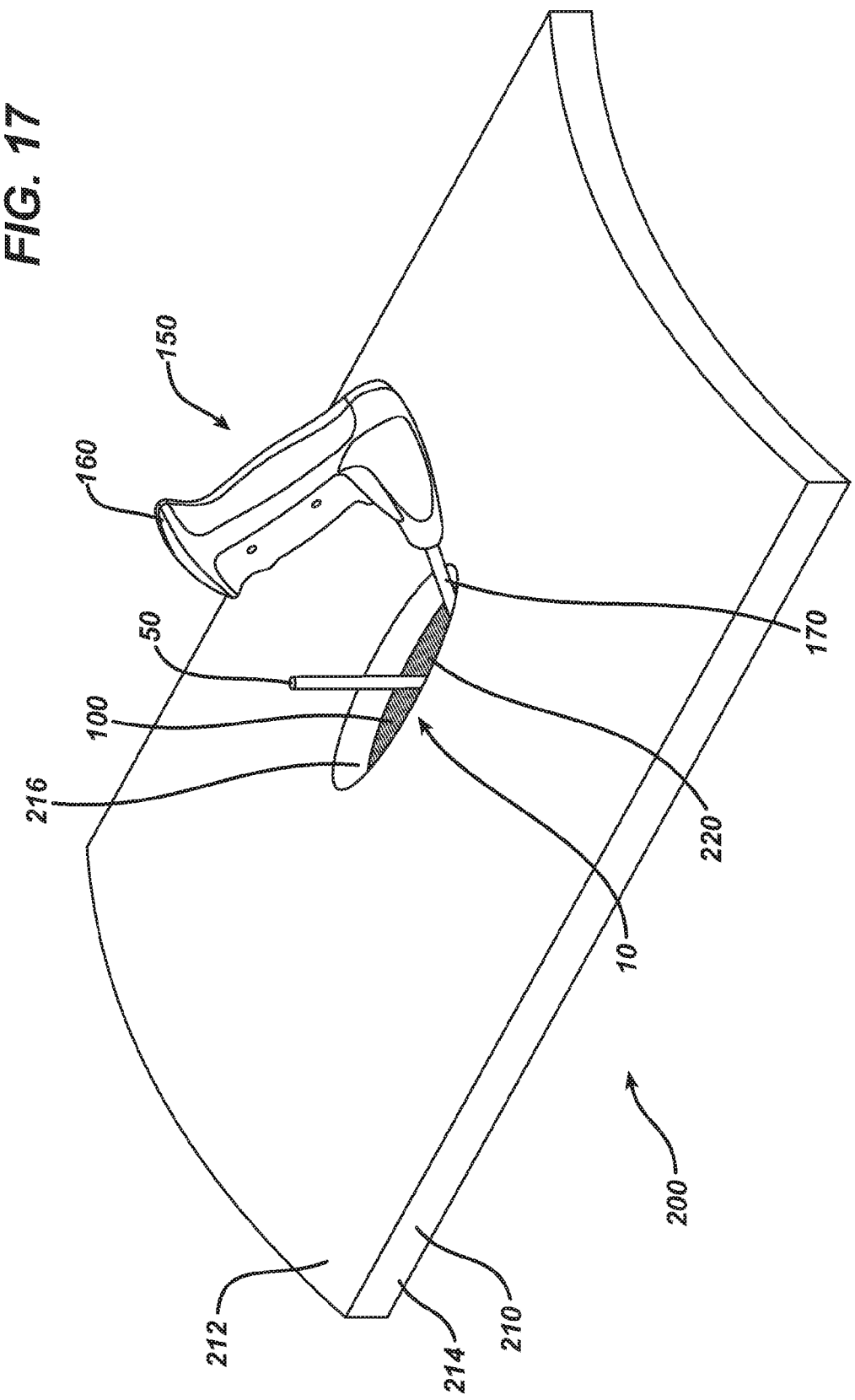
FIG. 17 is a perspective view illustrating a deployment device of the present invention engaged in the pocket of a surgical mesh inserted into a patient's body cavity; the shaft of a surgical tacking instrument is seen to be extending up through the opening in the patient's body wall.
Figure 18:
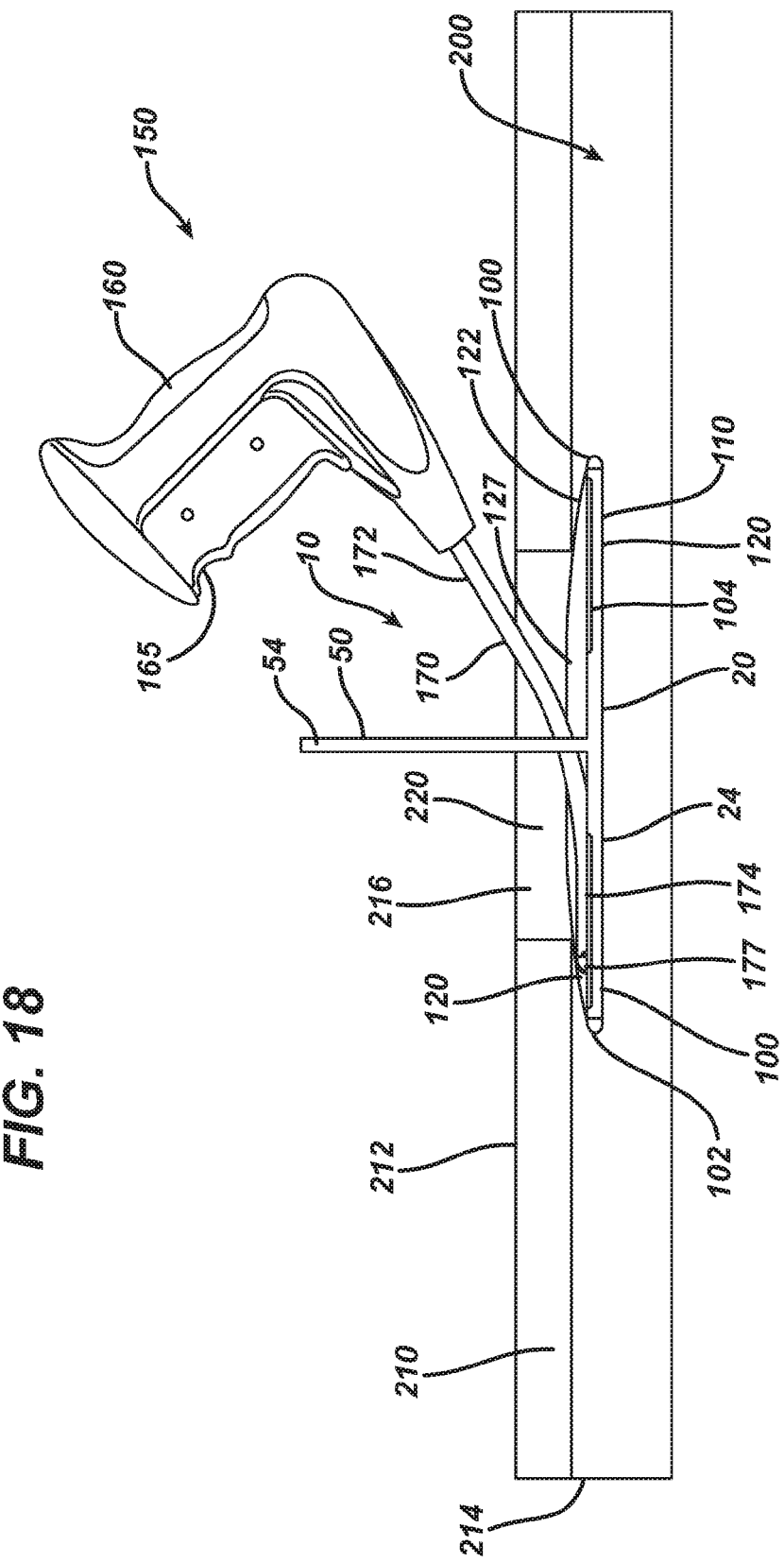
FIG. 18 is a cross-sectional view of the body wall of the patient of FIG. 16 showing the mesh positioned such that it is adjacent to the interior surface of the body wall with the distal end of the tacking instrument in position to tack the periphery of the skirt of the mesh to the tissue of the interior of the body wall.

FIGS. 17-18 illustrate the device 10 of the present invention deployed in the pocket of a mesh device 100 in a body cavity 200 of a patient. The body cavity 200 is surrounded by body wall 210 having top outer surface 212 and bottom interior surface 214. Opening 216 in outer surface 212 is seen to be over tissue defect 220 in body wall 210. The top mesh layer 120 of mesh implant 100 is seen to be deployed adjacent to the interior surface 214 of body wall 200. Manipulation handle 50 of deployment device 10 is seen to extend through defect 220 and opening 216. A section of shaft 170 of tacking instrument 150 extends through opening 216 and defect 220 and is guided in a channel 60 of planar member 20 toward the periphery 102 of mesh device 100. The distal end 174 of shaft 170 is seen to be positioned in channel 60 such that the discharge tip 177 is adjacent to stop wall 34 and positioned to secure skirt or top mesh 120 adjacent to the periphery 102 of mesh device 100.

The deployment devices 10 of the present invention may be utilized in surgical repair procedures to correct body wall defects in the following manner. A patient having a ventral hernia defect is prepared for surgery in a convention manner. The surgeon then initiates the surgical procedure by making an incision in the skin and subcutaneous tissue overlying the hernia. In the case of planned intra-peritoneal mesh placement, the hernia sac is opened. A suitably sized conventional ventral hernia mesh repair device is selected as the mesh tissue repair implant. An appropriately sized deployment device of the present invention is manipulated from an at-rest position to a deployment position by folding the planar member about its longitudinal axis. The planar member is then inserted through the top opening of the mesh device into the interior pocket, and moved to the at rest planar position, such that the rim of the deployment device is adjacent to the periphery of the mesh tissue repair implant. The mesh and deployment device are then handled as a system, folded along their respective axes, and inserted into the open space developed inside of the abdominal wall. The manipulation member can be used to position the mesh repair device about the hernia defect from the exterior of the patient. The manipulation member can also be pulled taut through the central opening to hold the mesh against the bottom interior surface of the abdominal wall by grasping and manipulating the manipulation member. A tacking instrument is then inserted into the mesh pocket through the top opening of the mesh device. The tip and shaft of the tacking instrument is guided into a groove in the top surface of the deployment device. Once the tip of the tacking instrument reaches the inner stop wall, the device is in the appropriate position relative to the periphery of the mesh. Manual counter pressure is applied to the top outer surface of the body wall and the tacking instrument is fired to deliver a fixation point through the mesh and into the interior layer of the abdominal wall (i.e. peritoneum and fascia). The tacking instrument is moved to an adjacent groove on the deployment device in order to ensure a second fixation point is applied a fixed distance away from the first fixation point, along the periphery of the mesh. Once the entire mesh is fixated about the periphery of the mesh device, the tacking instrument is removed. With the mesh fixated, the deployment aide is removed by bending it to remove the aide from the mesh. The skin incision is closed using appropriate suturing or closure techniques.

If desired, the deployment device may be left in the pocket of the mesh device after implantation and affixation, particularly if the deployment device is constructed of biodegradable polymers.

The following example is illustrative of the principles and practice of the present invention, although not limited thereto.

Example

A patient with a ventral hernia defect is prepared for an open hernia repair procedure in the following manner. The skin area surrounding the hernia is scrubbed with a conventional antimicrobial solution such as betadine. The patient is administered conventional general anesthesia in a conventional manner by induction and inhalation. An open surgical procedure is selected to repair the defect. The surgeon then initiates the surgical procedure by making an incision in the skin and subcutaneous tissue overlying the hernia. In the case of planned intra-peritoneal mesh placement, the hernia sac is opened. The edges of the healthy fascia around the defect are examined and any attachments of the viscera to the abdominal wall are divided to create a free space for fixation of the mesh.

The surgeon selects a suitably sized conventional hernia mesh patch device useful in an open ventral hernia repair procedure, wherein the mesh has an opening, a top layer forming a skirt and a pocket. An appropriately sized deployment device of the present invention is removed from its sterile packaging. The planar member of the device is manipulated from an at rest position to a deployment position by folding the planar member about its longitudinal axis. The planar member is then inserted through the top opening of the mesh device into the interior pocket, and moved to the at-rest planar position, such that the rim of the deployment device is adjacent to the periphery of the mesh implant device. The manipulation member of the deployment device projects through the opening to the exterior or the mesh and out through the opening in the abdominal wall.

The mesh and deployment device are then handled as a system, simultaneously folded along their respective axes, and inserted through the opening in the abdominal wall and into the open space developed inside of the abdominal wall. The central opening of the mesh is aligned with the incision made through the skin and abdominal wall using the manipulation member from the exterior of the patient. Stay sutures may optionally be placed through the mesh into the abdominal tissue as desired, i.e. at the four compass points of the mesh (North, South, East, and West). The mesh/deployment device system is aligned such that the manipulation member can be accessed through the central opening of the mesh, tissue defect, and skin incision. The manipulation member can be pulled taut to hold the mesh against the bottom interior surface of the abdominal wall.

A tacking instrument is then inserted into the mesh pocket. The tip and shaft of the tacking instrument are guided into a groove in the top surface of the deployment device. The tip follows the groove until it contacts the inner stop wall of the deployment device. Once the tip of the tacking instrument reaches this wall, the device is in the appropriate position relative to the periphery of the mesh. Manual counter pressure is applied to the top outer surface of the body wall and the tacking instrument is fired to deliver a fixation point through the mesh and into the interior layer of the abdominal wall (i.e. peritoneum and fascia). The tacking instrument is moved to an adjacent groove on the deployment aide in order to ensure a second fixation point is applied a fixed distance away from the first fixation point, along the periphery of the mesh. Once the entire mesh is fixated uniformly about its periphery, the tacking instrument is removed.

The deployment aide is then removed. With the mesh fixated, the deployment aide is removed by bending it to remove the aide from the mesh. The hernia defect may be primarily closed if desired. The skin incision is closed using appropriate suturing or closure techniques, and the incision is appropriately bandaged and the patient is moved to a recovery room.

The novel hernia repair devices and methods of the present invention have numerous advantages. The advantages include providing an adjunct device that allows a mesh tissue repair device to be manipulated from the exterior of the patient and fixated in a uniform manner about the periphery of the device using fasteners applied in a uniform manner about the periphery of the mesh implant device. By placing tacks with consistent spacing, the usage of tacks is optimized. Excessive tacks are avoided while ensuring that there are no excessive gaps between fixation points. Gaps can pose a risk to bowel entrapment. Another advantage is that the deployment aide is pliable and does not pose a risk of damaging the mesh repair device or the contents of the abdomen. The deployment aide also serves as a barrier to guide the tacking device upward toward the targeted tissue. The base of the deployment aide also serves as a barrier to shield viscera and abdominal contents from a tack or fixation point that may be accidentally delivered in the incorrect direction towards the viscera. This last point is important as a fixation point delivered toward the viscera may result in bowel perforation and a contaminated field.

Although this invention has been shown and described with respect to detailed embodiments thereof, it will be understood by those skilled in the art that various changes in form and detail thereof may be made without departing from the spirit and scope of the claimed invention.

We claim:

1. A deployment device for a tissue repair implant, comprising:
   a planar member, the planar member having a top surface, a bottom surface, and an outer periphery, a center and being capable of moving between a first at-rest position to a second deployment position;
   a rim member extending about the outer periphery, the rim member having a top, and inner stop wall, and an outer wall;
   a plurality of guide structures on at least a part of the top surface of the planar member and extending radially outward, wherein the guide structures comprise grooves extending into the top surface of the planar member, the grooves having bottoms, inner ends, outer ends, opposed sides and open tops, the grooves extending radially outward from the center to the rim member, wherein each groove has a passage for receiving at least part of a distal section of a surgical fastening instrument.

2. The device of claim 1, wherein the planar member additionally comprises a central opening.

3. The device of claim 1, wherein the planar member is foldable to place it in the deployment position.

4. The device of claim 1, additionally comprising a manipulation member extending up from the top surface of the planar member, wherein the manipulation member is selected from the group consisting of rods, tapes, finger grips, ropes, loops, handles, finger holes, and straps.

5. The device of claim 1, wherein the guide structures are evenly spaced along the periphery of the deployment device.

* * * * *